United States Patent [19]
Geringer

[11] Patent Number: 6,162,199
[45] Date of Patent: Dec. 19, 2000

[54] DEVICE FOR LOADING A SYRINGE FROM A VIAL

[76] Inventor: Joseph Robert Geringer, 36 Fairview Ave., Melrose, Mass. 02176

[21] Appl. No.: 09/493,376

[22] Filed: Jan. 28, 2000

Related U.S. Application Data

[60] Provisional application No. 60/154,797, Sep. 20, 1999.

[51] Int. Cl.[7] ........................................... A61M 5/00
[52] U.S. Cl. ............................ 604/208; 604/407; 141/27
[58] Field of Search ..................................... 604/181, 187, 604/207–210, 232, 218, 407; 141/26, 27

[56] References Cited

U.S. PATENT DOCUMENTS

| | | |
|---|---|---|
| 3,907,009 | 9/1975 | Dobbins . |
| 4,018,223 | 4/1977 | Ethington . |
| 4,098,276 | 7/1978 | Bloom et al. . |
| 4,219,055 | 8/1980 | Wright . |
| 4,274,453 | 6/1981 | Lee . |
| 4,778,454 | 10/1988 | LaDow . |

FOREIGN PATENT DOCUMENTS

| | | |
|---|---|---|
| 1179888 | 2/1970 | France . |

*Primary Examiner*—John D. Yasko
*Attorney, Agent, or Firm*—Vernon C. Maine; Scott J. Asmus

[57] ABSTRACT

A hand held device for loading a hypodermic syringe from a medicine vial is configured for easy placement of the syringe into a closely conforming channel in the proximal end of the device, with the needle end pointing towards the other end. The other end of the device is configured for easy placement of a standard vial into a closely conforming chamber with its penetrable cap facing the needle tip. Closing the device causes or permits the further action required for piercing the vial with the syringe needle. A sliding pull tab engages the syringe plunger so that gripping and pulling on the tab withdraws the plunger from the syringe, thus drawing fluid from the vial. An amplified or enhanced readout capability visually indicates the dosage of fluid withdrawn from the vial. An auxiliary needle mounted so as to be slightly offset from the syringe, provides for a supplemental piercing of the vial so that make-up air is available when large dosages are drawn from the vial with a single pull of the plunger.

9 Claims, 10 Drawing Sheets

DEVICE FOR LOADING A SYRINGE FROM A VIAL

CROSS REFERENCE TO RELATED APPLICATIONS

This application claims priority to pending U.S. application Ser. No. 60/154,797, filed Sep. 20, 1999 by the same applicant.

BACKGROUND OF THE INVENTION

1. Technical Field of the Invention

The present invention relates to aids for filling hypodermic syringes with fluid medications from vials with penetrable caps. In particular, it relates to a mechanical aid for enabling the easy introduction of the needle tip of a hypodermic syringe into a capped vial of liquid medication at the proper location in the cap, to the proper depth, and the subsequent loading of the syringe with the desired volume of medication for injection.

2. Background Art

Fluid medication for hypodermic injection is commonly packaged for dispensing in standard size vials or ampoules, the caps of which are penetrable by the needle tip of a syringe for loading the medication directly into the syringe. The typical syringe is configured with a transparent barrel, with markings indicating the volume of fluid contained in the barrel by the location or depth of the plunger in the barrel.

A skilled health care provider preparing to give an injection typically holds the vial between the thumb and forefinger or between the first two fingers of one hand, with the cap end of the vial in her palm. Holding the syringe in the opposite hand, with the syringe plunger fully depressed into the syringe, she skillfully introduces the needle tip into the vial. She then carefully supports the vial and syringe in their proper relationship and up ends the vial. She then withdraws the syringe plunger, drawing medication into the syringe until she sees by the barrel markings that the desired volume has been loaded into the syringe.

As is known on a practical level to syringe and vial users, and will be readily apparent to those familiar with the limitations presented by the relative compressibility of air and fluid, the volume of fluid that can be removed from the fixed volume of a vial before make-up air is admitted is limited. Small dosages in the order of 50 cubic centimeters may be readily withdrawn in a single draw. In order to draw significantly more fluid into a syringe, it is the practice to use the syringe to draw and inject sufficient makeup air into the vial to permit the fall loading of the required dosage.

There are many circumstances where on-demand or repetitive injections are necessary, making self administration of the injection the only practical means for getting a necessary and timely dose. The requisite skill for loading the syringe can be developed by people of average dexterity and eyesight, with practice. However, there is a large class of people less eager or less able to manipulate the vial and syringe in this manner, and desirous of a mechanical aid that would facilitate the process.

In the past, there have been numerous devices adapted specifically for facilitating the measurement of the dosage drawn into a hypodermic syringe. These inventions include those disclosed in the references to Dobbins, U.S. Pat. No. 3,907,009; Ethington, U.S. Pat. No. 4,018,223; Right, U.S. Pat. No. 4,219,055; Maaki, U.S. Pat. No. 4,252,159; LaDow, U.S. Pat. No. 4,778,454; Bloom, et al., U.S. Pat. No. 4,098,276; Strong, U.S. Pat. No. 4,883,101; Lee, U.S. Pat. No. 4,274,453; Walldbauer, Jr. et al, U.S. Pat. No. 3,833,030; French, GB Pat. No. 1,179,888; and Schraga, U.S. Pat. No. 5,697,916.

While various desirable objectives and useful features are dispersed throughout this and other prior art, including various brackets for holding vials and syringes, electronic displays of dosage amounts, and selectable or positionable levers for setting dosage amounts; nowhere is there known to be disclosed, illustrated or suggested a manually operable device that provides secure, semi-automatic positioning and insertion of the syringe needle into the vial by mere closure of a holding device, in combination with an enhanced grip for withdrawing the plunger and an enhanced visual indication of the volume of medication drawn.

SUMMARY OF THE INVENTION

The invention is fundamentally a device for facilitating the loading of a standard hypodermic syringe from a standard medicine vial with a penetrable cap. Different embodiments incorporate various novel combinations of features to satisfy the various objectives of the invention.

For example, it is an object of the invention to provide a device where the loading and closing of the device controls the relative position and orientation of the syringe and vial for automated positioning and piercing of the penetrable vial cap by the syringe needle tip, and for stable holding of the syringe and vial in the correct relative orientation during the loading.

It is a further object to provide that the syringe and vial are enclosed or semi-enclosed during the loading process, and in particular where the syringe needle tip is isolated during the piercing process from inadvertent touching by or pricking of the user's hand or fingers.

It is yet a further object to provide for an easily grasped or gripped, slidable pull tab mechanism that is engagable with the syringe plunger to provide a better grip for pulling the plunger for drawing the fluid.

It is still yet a further object to provide for enhanced readability of the volume of fluid being drawn into the barrel of the syringe, by use of a supplemental illumination source, an optical lens that amplifies the scale on the barrel, or by use of an electronic display unit and means for sensing the volume being drawn into the barrel and displaying the information on the display unit as illuminated or enlarged or both.

It is another object of the invention to provide means for admitting make-up air into the vial during a single loading pull on the syringe plunger, when dosages significantly more than about 50 cc's (cubic centimeters) are being drawn, such as by the use of an auxiliary hollow needle on a slider that provides for a auxiliary piercing of the vial in addition to the piercing by the syringe needle, so that make-up air can be drawn into the vial through the auxiliary needle as fluid is being drawn out into the syringe.

In accordance with the invention, the near or proximal end of a hand held device is configured for easy placement of the hypodermic syringe in a closely conforming longitudinal cradle or channel that assures the syringe is in a fixed position with the needle pointing towards the distal or forward end of the enclosure.

The forward or distal end of the device is configured for easy placement of a standard vial into a closely conforming longitudinally oriented cradle or chamber with the cap directed towards, but initially held clear of the needle tip.

Enclosing structure, where provided, is closed to further secure and isolate the syringe and vial. The closing motion causes or permits the further action required for piercing the vial with the syringe needle.

There is incorporated into the device a sliding grip component which, upon closure of the device, engages with the syringe plunger so that pulling aft on the grip withdraws the plunger from the syringe, thus drawing fluid from the vial.

A viewing system is incorporated into the device, providing an amplified or enhanced readout indicating the plunger position calibrated in standard units of volume, hence indicating the dosage of fluid withdrawn from the vial.

An auxiliary needle mounted so as to be slightly offset from the needle of the syringe when installed in the system, provides for a secondary piercing of the vial so that make-up air is available when that large dosages a drawn with a single pull.

Still other objects and advantages of the present invention will become readily apparent to those skilled in this art from the following detailed description, wherein I have shown and described only a preferred embodiment of the invention, simply by way of illustration of the best mode contemplated by me on carrying out my invention. As will be realized, the invention is capable of other and different embodiments, and its several details are capable of modifications in various obvious respects, all without departing from the invention.

DESCRIPTION OF THE PREFERRED EMBODIMENT

Reference is now made to FIGS. 1–8, which illustrate pictorially the various elements of the preferred embodiment of the invention.

Figure 1:
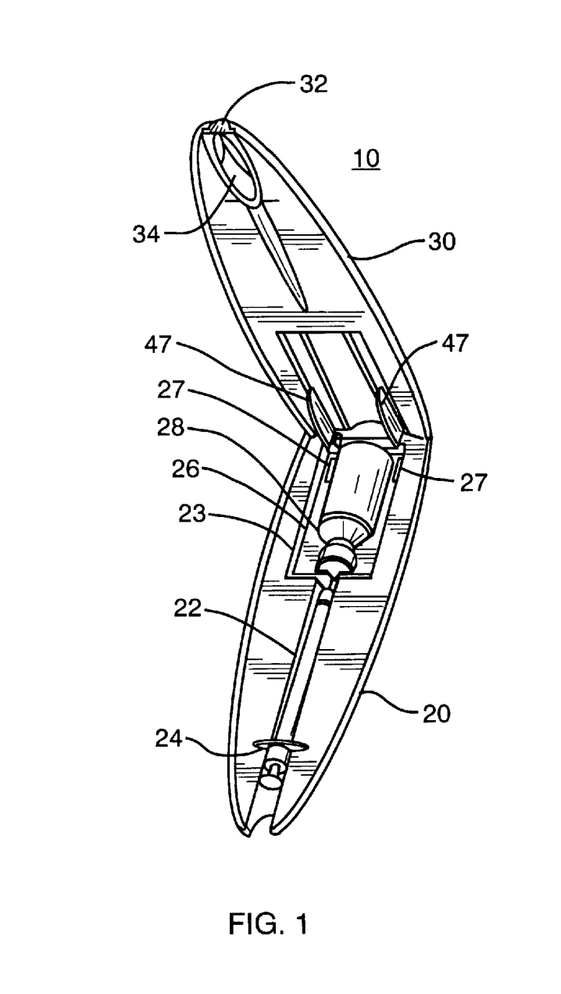
FIG. 1 is a perspective view of a first embodiment of the invention in the open position with vial and syringe emplaced.
Figure 2:
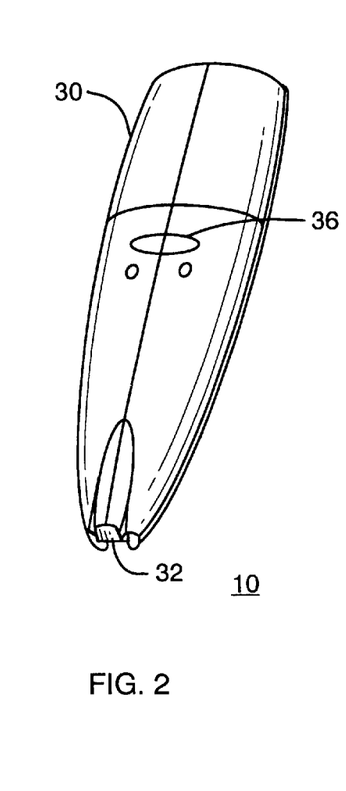
FIG. 2 is a perspective view of the embodiment of FIG. 1, in the closed position with the plunger pull tab in the no load or starting position.
Figure 3:
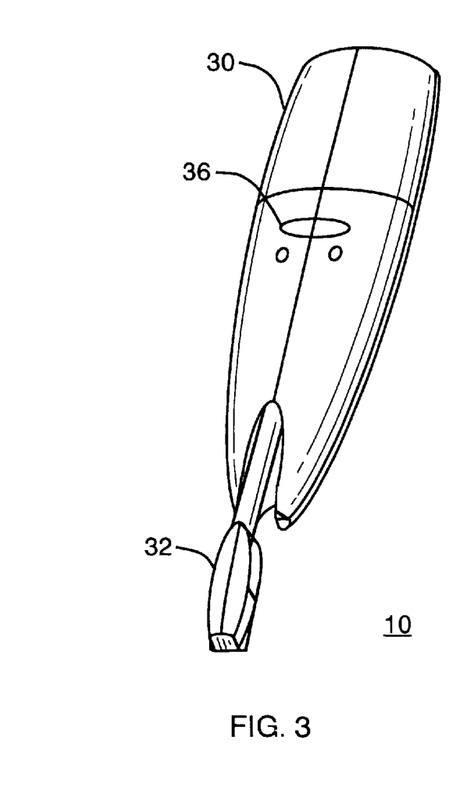
FIG. 3 is a perspective view of the embodiment of FIG. 2, in the closed position but with the plunger pull tab withdrawn as when the syringe is filled.
Figure 4:
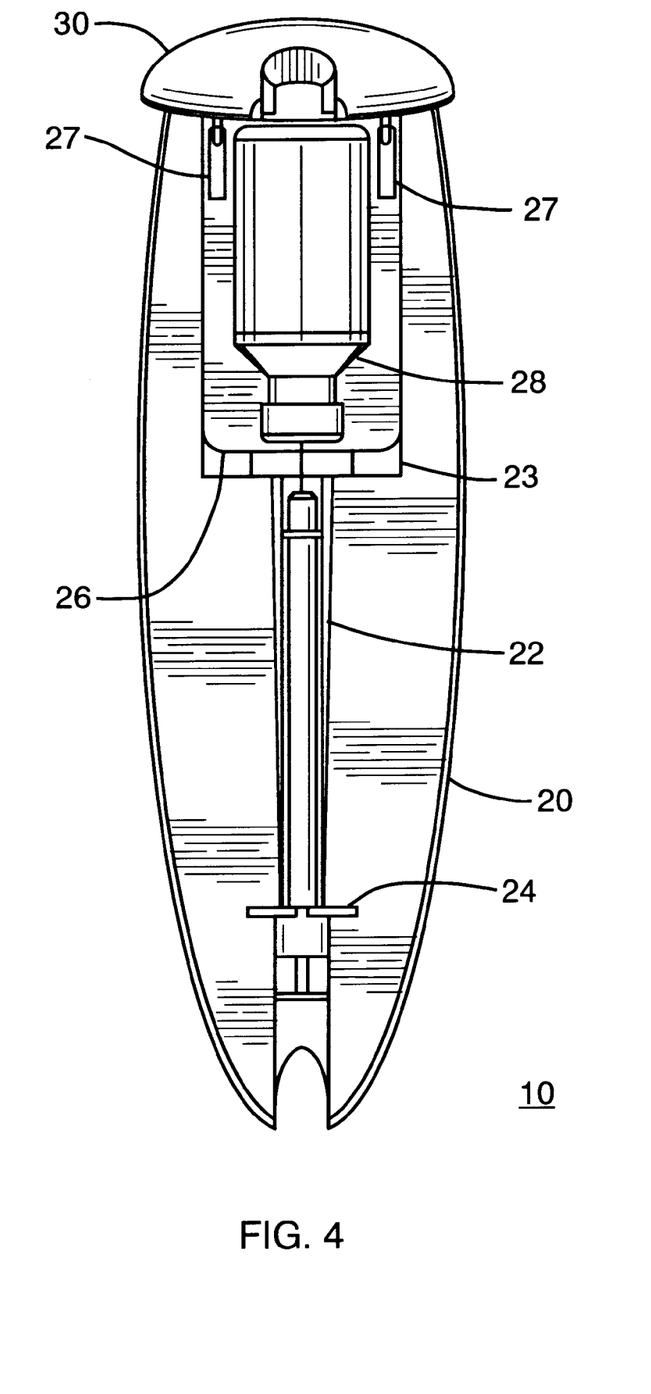
FIG. 4 is a top view of the embodiment of FIG. 1.
Figure 5:
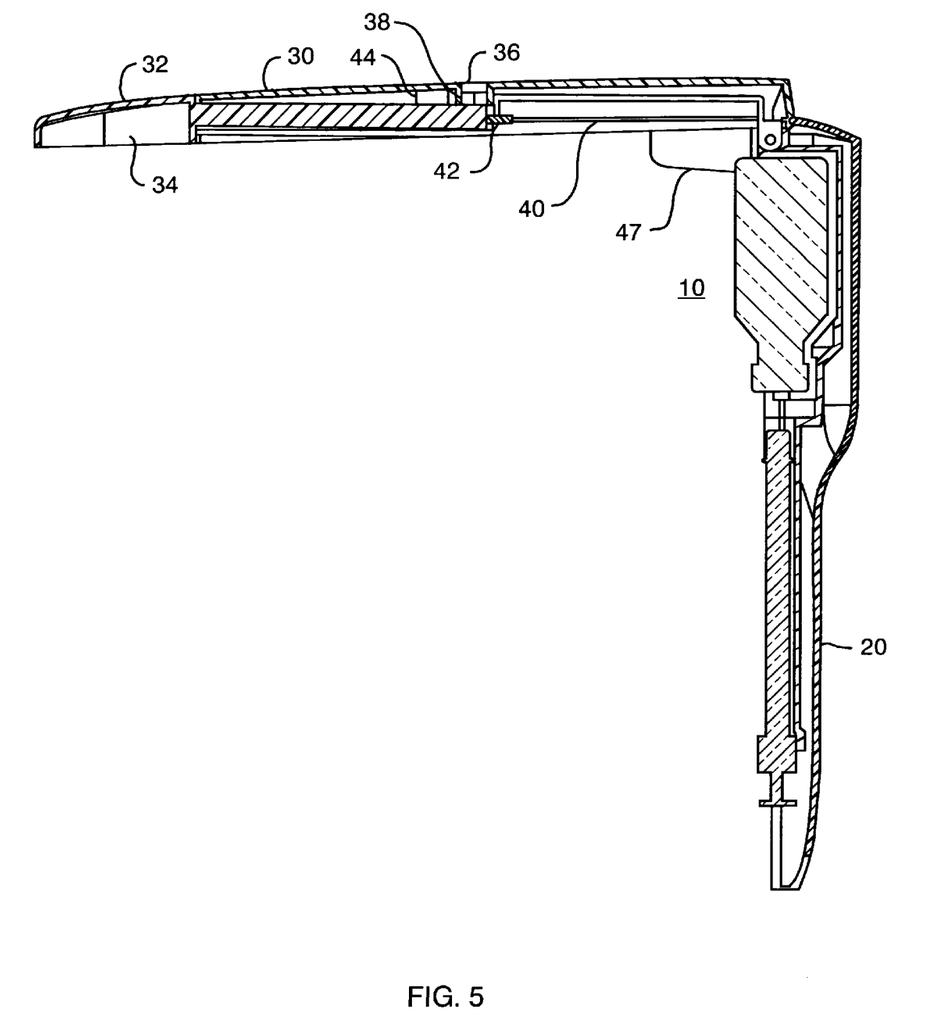
FIG. 5 is a side elevation cross section view of the embodiment of FIG. 1.
Figure 6:
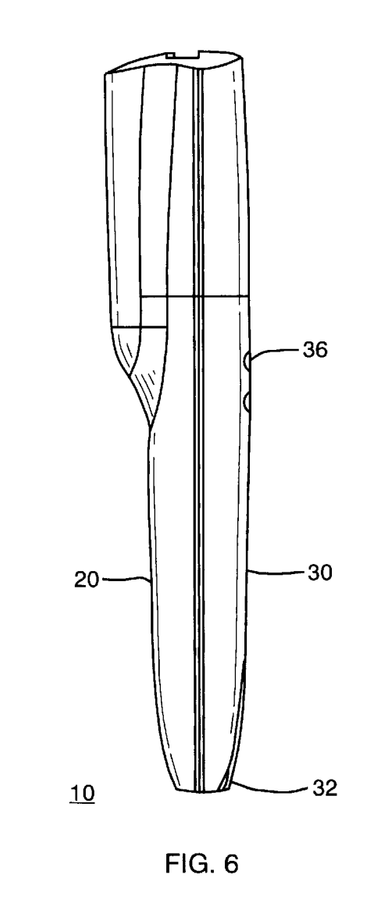
FIG. 6 is a side elevation of the embodiment of FIG. 2.
Figure 7:
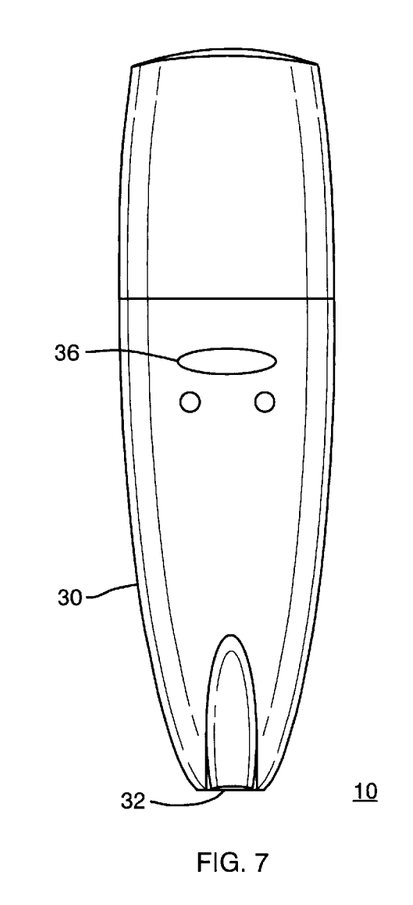
FIG. 7 is a top view of the embodiment of FIG. 2.
Figure 8:
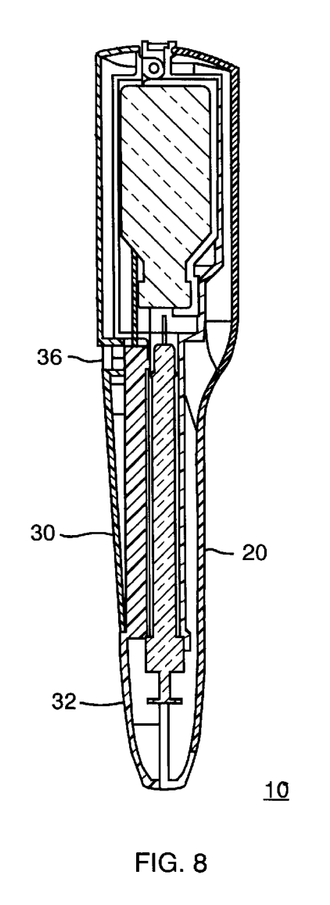
FIG. 8 is a side elevation cross section view of the embodiment of FIG. 2

Referring to FIG. 1, elongate enclosure 10, suitable in size for handheld use, has a base 20 and a conforming top 30, hinged at the forward end so as to open and close in a clam shell fashion. Axially disposed in base 20 is a syringe positioning channel 22, connecting to vial slider chamber 23 in which a vial slider 26 is configured for limited longitudinal travel within chamber 24, and spring loaded so as to be normally positioned away from syringe positioning channel 22. Vial slider 26 is incorporates a closely conforming vial pocket 28 in which a medication vial may be placed with its cap end facing aft towards syringe channel 22.

Channel 22 has an intersecting slot 24 near the aft end of the channel for receiving the holding flanges on the syringe barrel, so as to secure the syringe from fore and aft movement in the channel. Channel 22 is sufficiently shallow at the aft end that the end cap of the syringe plunger protrudes noticeably above the surface line of the channel.

Conforming top 30 incorporates longitudinally slidable syringe plunger pull tab 32, the aft or proximal end of which is easily gripped by the user for pulling out from enclosure 10 when the enclosure is closed. Pull tab 32 is configured with underside cavity 34, which when enclosure 10 is closed upon a syringe in syringe channel 22, effectively cages the protruding portion of the end cap of the syringe plunger so that pulling aft on pull tab 32 necessarily causes the plunger to be withdrawn from the syringe. A minor variation of this embodiment incorporates a simple racheting mechanism, not shown here, to provide an incremental, tactile clicking response to assist users in regulating the stroke of the plunger.

Top 30 also incorporates a top side numeric display window 36 for displaying the dosage loaded into the syringe, in conjunction with internal sensor system 38 for monitoring the position of the syringe plunger by which the dosage is calculated. An electronic embodiment of sensor system 38 utilizes a long, graduated strip 40, connected to pull tab 32, and passing through a pickup sensor 42, the linear displacement of the strip being the same as the plunger, the signal from which is converted by processor 44 to numerical data which is in turn displayed on a numeric LCD (liquid crystal display) array in window 36.

In another scheme for enhancing the user's ability to observe the volume of fluid being drawn into the barrel of the syringe, display window 36 is a simple lens beneath which strip 40 passes, enabling the user to directly read the graduations on the strip. The device can be configured, without inventive effort, to incorporate a supplemental, battery powered light source for illuminating the strip under window 36, to enhance the user's ability to observe the graduations.

In yet another variation of an enhansed display of dosage, window 36 is an elongated convex lens arranged to close over the graduated scale provided on the syringe barrel as the enclosure is closed, so the user can directly see the position of the plunger with respect to those graduations. As above, a supplemental, battery powered, light source can be incorporated into the unit to provide additional illumination of the amplified barrel graduations.

Referring again to FIGS. 1–8, vial slider 26 incorporates longitudinally oriented positioning cam lug slots 27 on either side of pocket 28. In the forward end of top 30, on the underside, slider positioning cam lugs 47 protrude downward so as to be engagable with slots 27 when top 30 is swung downward towards a closing position. The shape and effect of cam lugs 47 is that the closing of the top 30 on base 20 causes slider 26 to be pushed aft sufficiently far to impale the vial on the needle tip of the syringe, and when top 30 and base 20 are opened, allows slider 26 to be pushed forward by its slider spring (not shown), so as to disengage the vial from the syringe tip. So long as enclosure 10 is held open, slider 26 is held in position with its vial separated from the syringe needle tip, allowing the syringe to be removed without interference with the vial.

In operation, the user opens top 30 to expose syringe channel 22 and vial chamber 23. The vial slider 26 is drawn to its clearance position by the operation of lugs 47 in slots 27. A syringe is emplaced in the channel with its flanges nested into slot 24 and its needle tip pointed towards the vial chamber. A vial of medication such as insulin is placed into vial pocket 28, necessarily oriented with its cap directed towards the needle tip of the syringe. The closing motion of top 30 against base 20 encloses the syringe and the vial, and brings the slider towards the syringe so as to impale the cap on the needle tip.

Pull tab 32 is then grasped by the user and pulled back to draw fluid from the vial. The dosage is monitored at display window 36 while pulling, until the correct amount is loaded. The enclosure is then opened, disengaging the vial from the syringe so that the user can extract the syringe and the vial independently.

Figure 9:
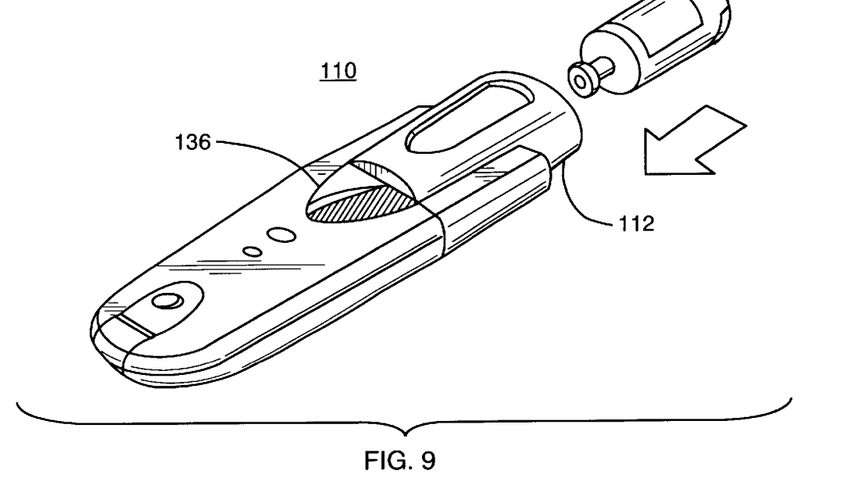
FIG. 9 is a perspective view of a second embodiment, utilizing an open end vial chamber and a sliding tray syringe carrier in the closed position.
Figure 10:
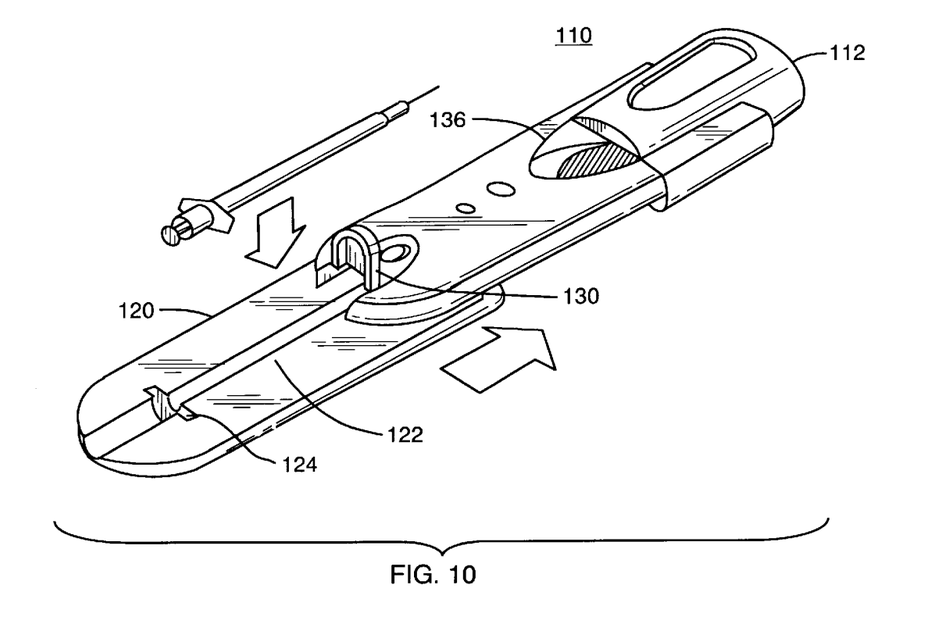
FIG. 10 is a perspective view of the embodiment of FIG. 9, with the syringe tray in the open position to expose the syringe mounting channel.
Figure 11:
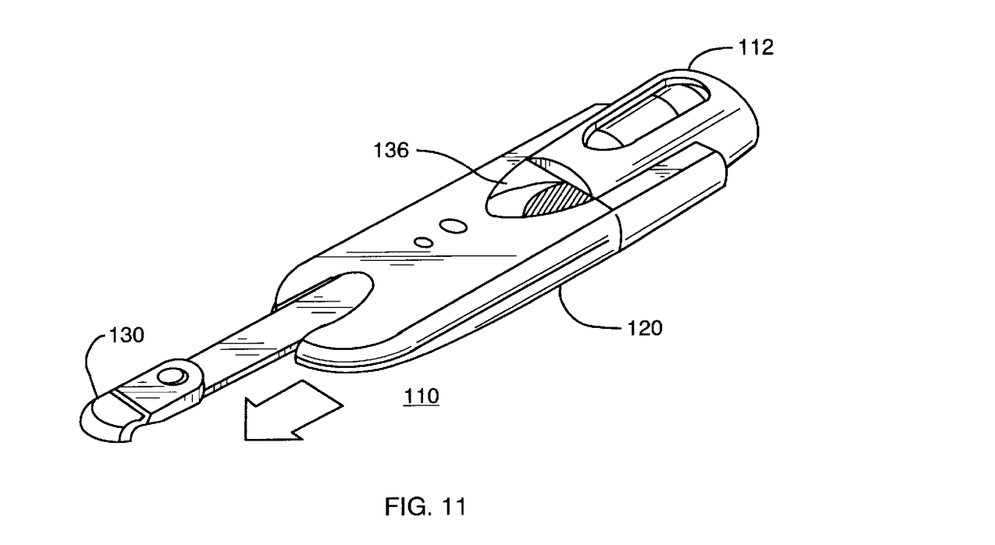
FIG. 11 is a perspective view of the embodiment of FIG. 9, with the pull tab extended as when a syringe has been fully loaded.

Referring now to FIGS. 9–11, another preferred embodiment consists of elongate enclosure 110 having a closely conforming vial chamber 112 open at its forward or distal end so as to receive a vial, such as an insulin vial, cap end first. A syringe tray 120 has a longitudinally oriented syringe channel 122 recessed into its upper surface for receiving a syringe with its needle pointing forward, with an intersecting slot 124 near the aft end of the channel for receiving the holding flanges on the syringe barrel, so as to secure the syringe from fore and aft movement on the slider. Tray 120 is slidingly attached to the underside aft end of enclosure 110 by a simple rail and groove arrangement so as to be slidable in the aft direction to expose channel 122 for placement of a syringe, and in the forward direction to carry the syringe fully into enclosure 110 and into piercing contact with the vial.

Enclosure 110 incorporates a plunger positioning handle or pull tab 130, and a dosage display window 136, and related internal elements, which consist of and perform similar to the analogous structure of the embodiment of FIGS. 1–8.

In operation, the vial is inserted cap end first into the vial chamber 112. The slide tray 120 is slipped back to expose the syringe channel 122, into which a syringe is inserted so that its flanges are engaged in slot 124. The closure or forward sliding action of slide tray 120 causes the needle tip of the syringe to pierce the cap of the vial to just the right depth. The user then draws back on pull tab 130, reading the volume at display window 136, until the correct dosage is drawn.

Figure 12:
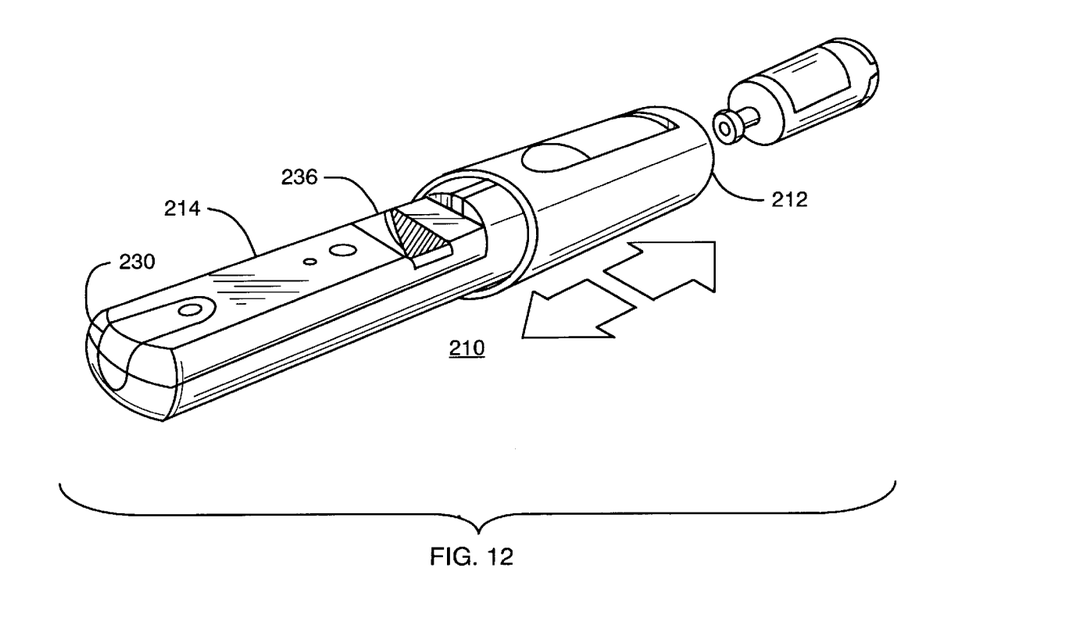
FIG. 12 is a perspective view of a third embodiment of the invention, utilizing an open end vial chamber and a hinged tray top in the closed position.
Figure 13:
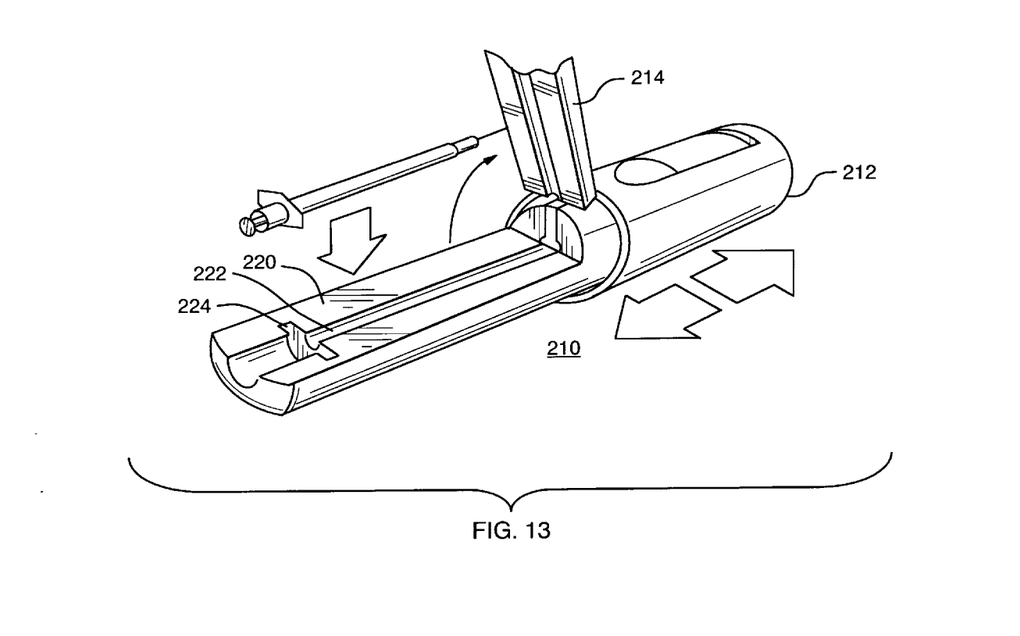
FIG. 13 is a perspective view of the embodiment of FIG. 12, with the hinged tray top shown in the open position.
Figure 14:
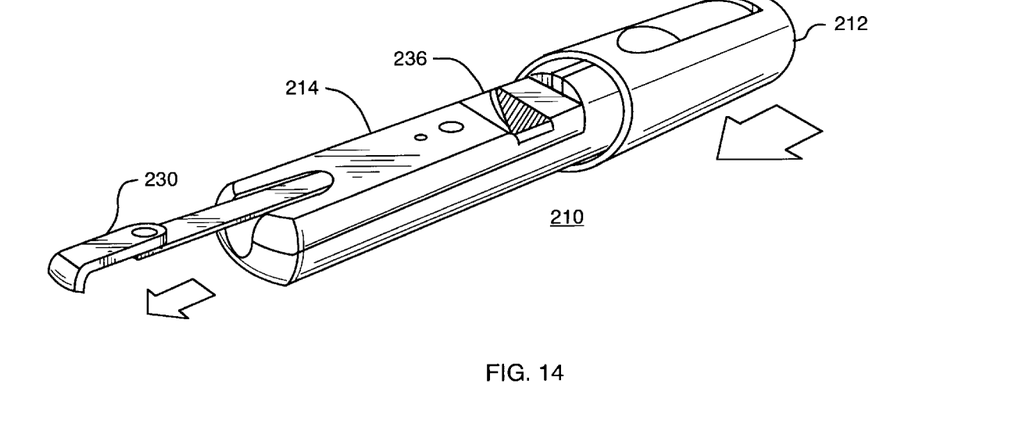
FIG. 14 is a perspective view of the embodiment of FIG. 12, with the hinged tray top in the closed position and the pull tab fully extended.

Referring to FIGS. 12–14, yet another preferred embodiment consists of enclosure 210, having a closely conforming slidable vial chamber 212 open at its forward or distal end so as to receive a vial, cap end first. There is recessed into surface 220 a longitudinally oriented syringe channel 222 for receiving a syringe with its needle pointing forward. Channel 222 has an intersecting slot 224 near the aft end of the channel for receiving the holding flanges on the syringe barrel, so as to secure the syringe from fore and aft movement in the channel. Tray top 214 is hinged to enclosure 210 just aft of vial chamber 212, fits conforming over a syringe in channel 222 when closed and opens upward and forward to expose syringe tray surface 220 and inhibit aft sliding movement of vial chamber 212.

Tray top 210 incorporates a plunger positioning pull tab 230, and a dosage display window 236, and related internal elements, which consist of and perform similar to the analogous structure of the embodiment of FIGS. 1–8. Tray top 214 is closable over the syringe against surface 220, in the manner of the closure of the previous embodiments, but permitting in this embodiment, when fully closed, the aft sliding of vial chamber 212 so as to bring the vial into piercing contact with the needle tip of the syringe. The vial chamber must be likewise slide forward, disengaging the vial from the syringe, before tray top 214 can be opened to remove the syringe.

In operation, a vial is inserted, cap end first into slidable vial chamber 212. Hinged tray top 214 is opened up to expose the syringe channel, and in the opening motion pushes back and then holds back the slidable vial chamber so that the vial is clear of where the syringe position. The syringe is then emplaced in channel 222, with its flanges installed in slot 224 so as to prevent sliding of the syringe in the channel. Tray top 214 is then closed over the syringe, permitting the slidable vial chamber and vial to be slid towards the syringe, impaling the vial cap on the needle point. Pull tab 230 is then operated as before, and the dosage is read at display window 236.

Figure 15:
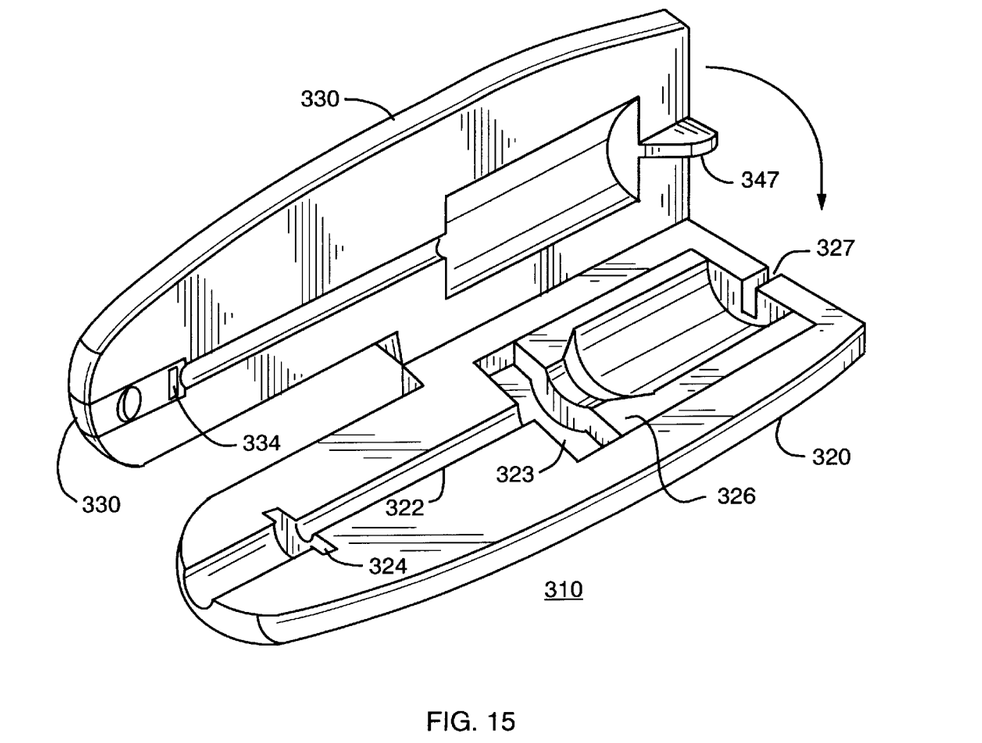
FIG. 15 is a perspective view of a fourth embodiment of the invention, with a side hinged base and top.

Referring now to FIG. 15, elongate enclosure 310 has a base 320 and a conforming top 330, hinged together at one side so as to open and close in a clam shell fashion. Axially disposed in base 320 is a syringe positioning channel 322, connecting to vial slider chamber 323 in which a vial slider 326 is configured for limited longitudinal travel within chamber 323. Vial slider 326 incorporates a closely conforming vial pocket 328 in which a medication vial may be placed with its cap end facing aft towards syringe channel 322. Channel 322 has an intersecting slot 324 near the aft end of the channel for receiving the holding flanges on the syringe barrel, so as to secure the syringe from fore and aft movement in the channel. Channel 322 is sufficiently shallow at the aft end that the end cap of the syringe plunger protrudes noticeably above the surface line of the channel.

Conforming top 330 is configured to close over a vial and syringe when emplaced in base 320, and incorporates longitudinally slidable syringe plunger pull tab 332, the aft or proximal end of which is easily accessible by the user for pulling out from enclosure 310 when the enclosure is closed. Pull tab 332 is configured with underside cavity 334, which when enclosure 310 is closed upon a syringe in syringe channel 322, effectively cages the protruding portion of the end cap of the syringe plunger so that pulling aft on pull tab 332 necessarily causes the plunger to be withdrawn from the syringe.

Top 330 also incorporates a top side numeric display window 336 and related structure, not shown here but similar in form and function to previous embodiments, for displaying the dosage loaded into the syringe.

Base 320 incorporates a longitudinal slot 327, communicating with slider chamber 323. In the forward end of top 330, on the underside, slider positioning lug 347 protrudes downward so as to be engagable with slot 327 and in contact with slider 326 when the enclosure is closed. The shape and effect of lug 347 is that the closing of the top 330 on base 320 causes slider 326 to be pushed aft sufficiently far to impale the vial on the needle tip of the syringe. Operation of this embodiment is analogous to the embodiment of FIGS. 1–8, except for the side hinged top and base.

Figure 16:
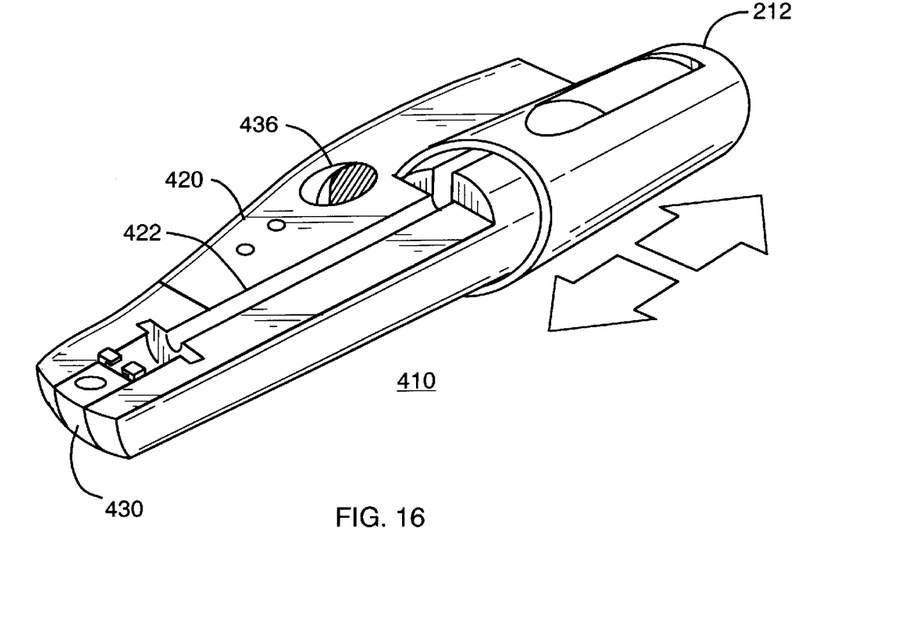
FIG. 16 is a perspective view of a fifth embodiment of the invention, with a slidable vial chamber and an exposed syringe channel, with the pull tab mechanism installed below the syringe channel and the display window offset to one side of the syringe channel.
Figure 17:
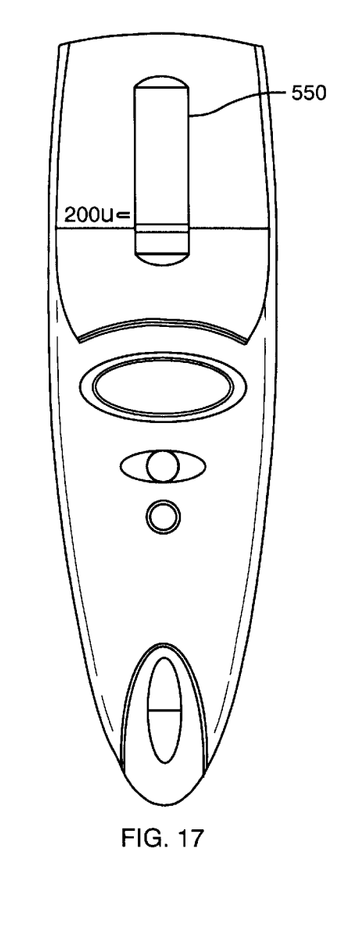
FIG. 17 is a top front view of a sixth embodiment of the invention.
Figure 18:
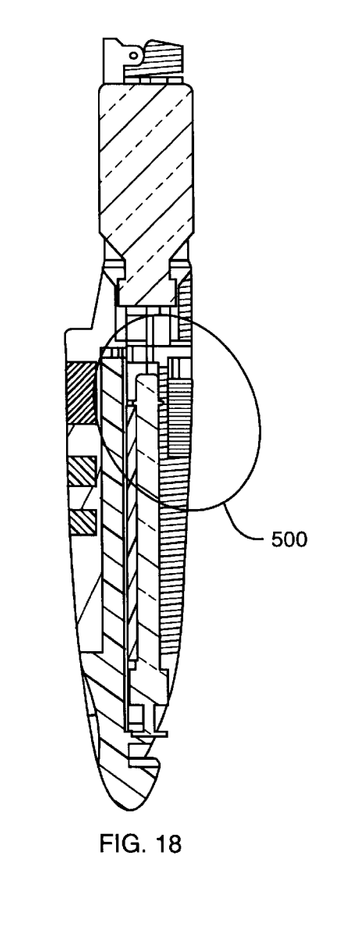
FIG. 18 is a cross section side elevation of the embodiment of FIG. 17, with auxiliary needle and needle slider revealed.
Figure 19:
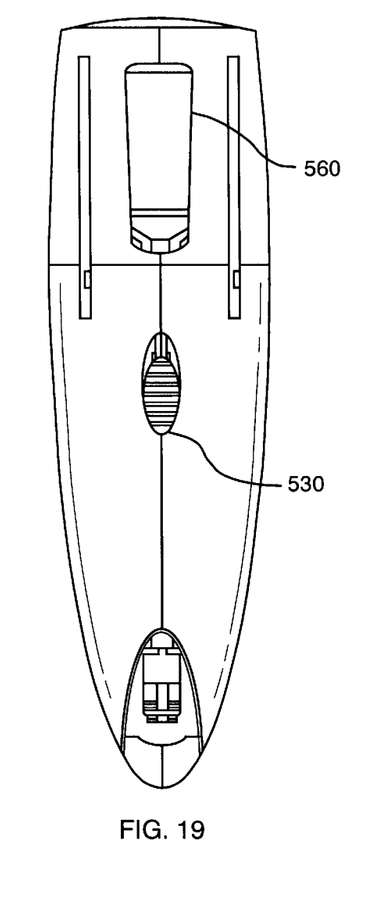
FIG. 19 is a bottom side view of the embodiment of FIG. 17, with auxiliary needle slider grip revealed.
Figure 20:
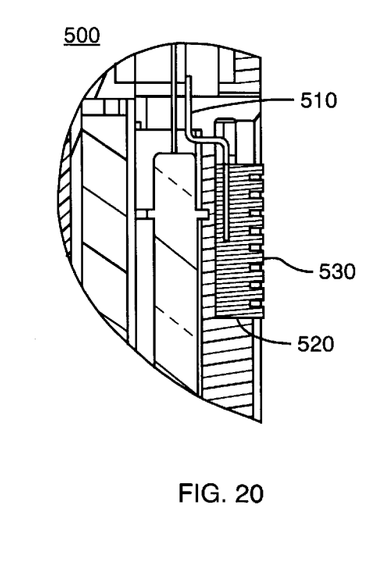
FIG. 20 is a partial close up of the view of FIG. 18, with auxiliary needle and needle slider revealed in greater detail.

Referring now to FIG. 16, there is still yet another preferred embodiment, a semi enclosed unit 410, incorporating the slidable vial chamber 212 of the embodiment of FIGS. 12–14, but having an exposed tray surface 420, below which is incorporated a plunger positioning pull tab 430 exposed at the aft end of unit 410 for access, with related internal elements which consist of and perform similar to the analogous structure of the embodiment of FIGS. 1–8, except that dosage display window 436 is laterally displaced from channel 422 on tray surface 420. A simple mechanical interlock (not shown) must be actuated by inserting a syringe into channel 422, to enable slidable vial chamber 412 to be pushed aft into piercing contact with the needle of the syringe.

The operation of this embodiment is distinguished from the other embodiments by the syringe remaining substantially exposed, although the needle and the vial are still fully enclosed. The pull tab engages the syringe plunger from underneath, and the display window and associated components are mounted in the base rather than the top or closing member.

Referring now to FIGS. 17–20, an embodiment functionally similar to the embodiment of FIGS. 1–8 includes an extra function, a make-up air mechanism 500, consisting in this embodiment of auxiliary hollow needle 510 attached to auxiliary needle slider 520. The aft or proximal end of the needle is vented to atmosphere. The distal end and point of needle 510 are configured to be parallel to but offset from the needle of a syringe when installed in the system. The amount of offset between the syringe needle and the auxiliary needle is sufficient to provide clearance from the syringe, and still be within the diameter of the penetrable portion of the vial cap.

Slider 520 is configured for limited longitudinal movement so as when in the aft position to hold needle 510 clear of the vial top and the syringe so that vials and syringes can be installed and used without interference with or from auxiliary needle 510, for drawing and loading relatively small dosages not requiring the admission of makeup air into the vial.

Slider grip 530 on the underside of slider 520 is exposed through a port on the underside of the case for access and operation by the user to advance and retract the auxiliary needle into the vial top when a vial is present, to permit the makeup air to be drawn into the vial when the syringe plunger is withdrawn for a relatively larger dose.

Slider 520 is mechanically interlocked with the case cover such that the cover may not be opened accept when the slider is in the aft position with the auxiliary needle held clear of the vial top. The assemblage of auxiliary needle 510 and slider 520 are easily removable and replaceable so as to provide for disposal and replacement as required. Make-up air mechanism 500 is adaptable to the various preferred embodiments of the invention.

The cover and case of this embodiment are further equipped with vial chamber viewing ports 550 and 560 respectively, through which the volume of fluid in the vial may be readily detected by the user. This feature is likewise adaptable to other embodiments to provide the same functionality.

To those skilled in the art, the invention and the many embodiments all admit of further variations. For example, the viewing scheme may incorporate optical encoder or magnetic sensing technology, powered by a battery, to detect the position of the sliding member or strip attached to the pull tab. Electronic versions may have on/off control switches or buttons, and a calibration or zeroing button that sets the display at zero for the plunger starting position.

There may be further incorporated into the unit, a digitizer circuit and connector to enable remote sensing of the dosage, and/or recording circuitry, to enable storage and later retrieval of the dosage. A keypad may mounted or attached, to facilitate the recording of related information such as the date, time, type of medication, and the identification of the administrator and receptor of the dose, for later manual or automated transfer to a suitable information repository, electronic or otherwise.

As another example, the vial slider may be motorized, with appropriate controls, rather than positioned by the slot and cam lug interaction upon closing scheme as described for the preferred embodiment.

The above illustrated and described embodiments share the common traits of the invention. The respective orientation and position of the syringe and vial is controlled by the device. The insertion of the needle into the vial takes place within a secure enclosure, and is mechanically actuated within the device so as to remove the uncertainty of manual insertion.

The pull tab provides a more certain grasp and control of the plunger with the thumb and first finger of one hand on the pull tab, with respect to a more certain grip with the other hand on the device, rather than holding the loosely coupled syringe and vial combination aloft and in their proper relationship as in the traditional manual technique. The display window provides an enhanced view of the dosage as it is being drawn, as compared to directly reading the graduations on the barrel of the syringe.

The objects and advantages of the invention may be further realized and attained by means of the instrumentalities and combinations particularly pointed out in the appended claims. Accordingly, the drawing and description are to be regarded as illustrative in nature, and not as restrictive.

What is claimed is:

1. A handheld device for loading a syringe with fluid from a vial with a penetrable cap, comprising
   an elongate base with a syringe channel axially aligned with and communicating with a vial chamber,
   a vial slider slidably installed within said vial chamber and configured with an open face vial pocket, said vial pocket configured for holding a said vial with its said penetrable cap oriented towards said syringe channel, means for securing a syringe longitudinally within said syringe channel with its syringe needle tip oriented towards said vial chamber, an elongate top hingedly attached to said base for closure thereon so as to secure a said syringe in said channel and a said vial in said vial pocket, said top having means for engaging said vial slider and causing sliding motion of said vial slider towards said channel while said top is being closed, said sliding motion of said vial slider impaling said vial through said penetrable cap with said syringe needle tip, enhanced means for gripping the plunger of the syringe for pulling so as to draw said fluid from said vial into the barrel of said syringe, enhanced means for observing the volume of said fluid drawn into said barrel, and means for observing the volume of said fluid remaining in said vial.

2. The handheld device for loading a syringe of claim 1, said enhanced means for gripping the plunger comprising a slidable pull tab mechanism with proximal end gripping surface, said mechanism being engagable with said plunger for pulling.

3. The handheld device for loading a syringe of claim 2, said means for securing, a syringe in the channel comprising a closely conforming syringe flange slot intersecting said syringe channel so as to accept the flanges of said syringe, thereby defining the position of a said syringe within the length of said channel.

4. The handheld device for loading a syringe of claim 1, said means for engaging at least one cam lug protruding downward and located so as to contact and push said slider towards said syringe channel when said top is in closing motion.

5. The handheld device for loading a syringe of claim 4, said slider having two longitudinal slots, one on each side of said vial pocket, said at least one cam lug being two lugs positioned so as to each engage a respective said slot and jointly push said slider towards said syringe when said top is in said closing motion.

6. The handheld device for loading a syringe of claim 1, said enhanced means for observing the volume of fluid drawn comprising a port in said top through which the volumetric scale on said barrel is visible.

7. The handheld device for loading a syringe of claim 1, said enhanced means for observing the volume of fluid drawn comprising an electronic display unit and means for sensing said volume and presenting said volume thereon.

8. The handheld device for loading a syringe of claim 1, further comprising means for admitting make-up air into said vial during said loading.

9. The handheld device for loading a syringe of claim 10, said means for admitting make-up air into said vial during loading comprising a hollow auxiliary needle securely mounted in a needle slider and oriented so as to be clear of said vial when in a retracted position and to pierce said vial when advanced to a forward position, the aft end of said auxiliary needle being open for admitting air.

\* \* \* \* \*